United States Patent
He et al.

(10) Patent No.: US 6,584,266 B1
(45) Date of Patent: *Jun. 24, 2003

(54) CHROMOPHORES FOR POLYMERIC THIN FILMS AND OPTICAL WAVEGUIDES AND DEVICES COMPRISING THE SAME

(75) Inventors: Mingqian He, Painted Post, NY (US); Thomas M. Leslie, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 157 days.

This patent is subject to a terminal disclaimer.

(21) Appl. No.: 09/595,221

(22) Filed: Jun. 16, 2000

(51) Int. Cl.$^7$ .............................. G02B 6/10; B32B 27/00
(52) U.S. Cl. ...................... 385/130; 385/142; 385/143; 252/582; 428/412; 428/423.1; 428/473.5
(58) Field of Search ................................. 385/129, 130, 385/141–143; 428/412, 423.1, 473.5; 252/582, 583, 586

(56) References Cited

U.S. PATENT DOCUMENTS

| | | | |
|---|---|---|---|
| 4,014,951 A | 3/1977 | Näf et al. ............... | 585/600 |
| 4,767,169 A | 8/1988 | Teng et al. | |
| 4,795,664 A | 1/1989 | DeMartino | |
| 4,810,338 A | 3/1989 | DeMartino et al. | |
| 4,936,645 A | 6/1990 | Yoon et al. | |
| 5,006,285 A | 4/1991 | Thackara et al. | |
| 5,044,725 A | 9/1991 | DeMartino et al. | |
| 5,106,211 A | 4/1992 | Chiang et al. | |
| 5,133,037 A | 7/1992 | Yoon et al. | |
| 5,170,461 A | 12/1992 | Yoon et al. | |
| 5,187,234 A | 2/1993 | Leslie et al. | |
| 5,196,509 A | 3/1993 | Allen | |
| 5,247,042 A | 9/1993 | Allen et al. | |
| 5,290,630 A * | 3/1994 | Devonald et al. ........... | 428/333 |
| 5,326,661 A | 7/1994 | Sansone et al. | |
| 6,057,316 A | 5/2000 | Wrobel et al. ............ | 514/224.5 |
| 6,067,186 A | 5/2000 | Dalton et al. ............. | 359/321 |
| 6,114,031 A * | 9/2000 | Roberts et al. ............ | 428/333 |

FOREIGN PATENT DOCUMENTS

| | | |
|---|---|---|
| JP | 3-101671 A | 4/1991 |
| WO | WO 98/56749 | 12/1998 |

OTHER PUBLICATIONS

Advanced Organic Chemistry, 3$^{rd}$ Ed., Jerry March, 1985, Table 1, pp. 220–222.

Melikian et al., "Synthesis of Substituted Dicyanomethylendihydrofurans," *Synthetic Communications*, 25(19):3045–3051 (1995).

Wang et al., "Design, Synthesis and Characterization of a Novel Substituted Dicyanomethylendihydrofuran Based High–β NLO Chromophore and Its Polymers with Exceptionally High Electro–Optic Coefficients," *Polymer Preprints*, 39(2):1065–1066 (Aug. 1998).

Zhang et al., "A Novel Trilinkable High μβ NLO Chromophore for Polymeric Electro–optic Material With Enhanced Thermal Stability," *Polymer Preprints*, 40:156–157 (1999).

Ren et al., "A Trifunctionalized High μβ Chromophore and Its 3D Polyurethane Network With Enhanced NLO Alignment Stability for Electro–optic Device Applications," *Polymer Preprints*, 40:160–161 (1999).

Ren, "Electro Active Polymer Thin Films for Fabrication of Ultra–high Bandwidth Integrated Electro–optic Modulators," Ph.D. Thesis, University of Southern California (Aug. 1999).

Todorova et al., "New NLO Chromophores Based on 2–amino–1,1,3–tricyano–1–propene Acceptor," *Polymeric Materials: Science and Engineering*, 83:256–257 (Aug. 2000).

Reddy et al., "Vilsmeier Reaction on Some 6 & 7–Methoxy–1–tetralols," *Indian Journal of Chemistry*, 20B:100–103 (Feb. 1981).

* cited by examiner

Primary Examiner—John D. Lee
(74) Attorney, Agent, or Firm—Angela N. Nwaneri; Walter M. Douglas; Braman & Rogalskyj, LLP

(57) ABSTRACT

The present invention is directed to chromophores having novel electron withdrawing groups and novel bivalent cyclic bridges and to optical waveguides and optical devices having polymeric thin films which contain the novel chromophores.

68 Claims, No Drawings

CHROMOPHORES FOR POLYMERIC THIN FILMS AND OPTICAL WAVEGUIDES AND DEVICES COMPRISING THE SAME

FIELD OF THE INVENTION

The present invention relates to chromophores which can be used in the preparation of polymeric thin films for waveguide media, and to optical waveguides and devices comprising the chromophores.

BACKGROUND OF THE INVENTION

Thin films of organic or polymeric materials with large second order nonlinearities in combination with silicon-based electronic circuitry can be used in systems for laser modulation and deflection, information control in optical circuitry, as well as in numerous other waveguide applications. In addition, novel processes through third order nonlinearity such as degenerate four-wave mixing, whereby real-time processing of optical fields occurs, have utility in such diverse fields as optical communications and integrated circuit fabrication. The utility of organic materials with large second order and third order nonlinearities for very high frequency application contrasts with the bandwidth limitations of conventional inorganic electrooptic materials currently in use.

Numerous optically responsive monomers and polymers have been developed for use in organic materials which, in turn, can be used in the waveguide applications described above. For example, U.S. Pat. No. 5,044,725, which is incorporated herein by reference in its entirety, describes numerous polymer compositions which provide suitable nonlinear optical response. U.S. Pat. No. 5,044,725 describes, for example, a preferred polymer composition comprising an organic chromophore containing an electron donating group and an electron withdrawing group at opposing termini of a bridge.

Synthesis of high performance organic, high $\mu\beta$ electro-optic chromophores must be accomplished in order to make polymer-based electro-optic waveguides and devices. The synthesis of electro-optic chromophore bridge compounds and donor-bridge compounds for organic nonlinear optical applications are generally known in the art. Although some chromophores have been reported in the literature, many of them have showed several and sometimes severe problems ranging from thermal instability, insolubility in the polymer, photodegradability, exhibition of a broad absorption band into the wavelength region of interest, and large birefringence upon poling. Accordingly, suitable electro-optic chromophores are desired.

SUMMARY OF THE INVENTION

The present invention is directed, in part, to compounds which can serve as chromophores in, for example, thin films for optical waveguides and optical devices.

Preferred compounds of the invention comprise novel electron withdrawing groups and have Formula I:

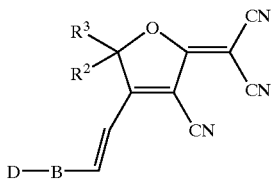

wherein D is an electron donating group; B is or contains at least one bivalent aromatic ring; and $R^2$ and $R^3$ each, independently, are either H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocyclic, substituted or unsubstituted heterocyclic, substituted or unsubstituted cyclohexyl, or $(CH_2)_n$—O—$(CH_2)_n$, where n is 1–10. Alternatively, $R^2$ and $R^3$ together form a ring structure or a substituted ring structure.

In other embodiments of the invention, the chromophores comprise novel cyclic bridges comprising at least one bivalent aromatic ring. Preferred compounds of the invention have Formula II:

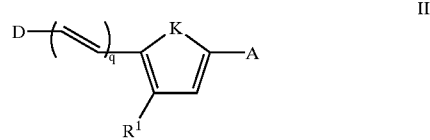

wherein D is an electron donating group; A is an electron withdrawing group; K is O or S; $R^1$ is —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q is absent, O or S; and q is 1, 2, or 3.

Other preferred compounds of the invention have Formula III:

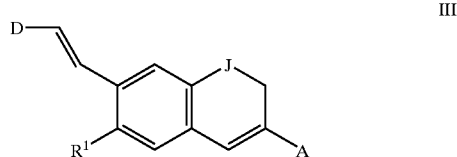

wherein D is an electron donating group; A is an electron withdrawing group; J is $CH_2$, O or S; $R^1$ is —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q is absent, O or S, In other embodiments of the invention, the chromophores comprise novel cyclic bridges comprising at least one bivalent or conjugated ring structure, such as an aromatic ring, and novel electron withdrawing groups. Preferred compounds of the invention have Formula IV:

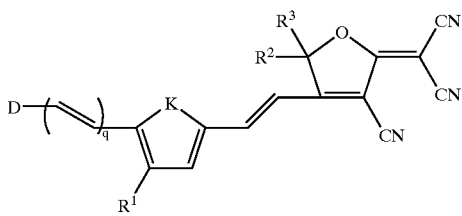

IV wherein D is an electron donating group; K is O or S; $R^1$ is —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q is absent, O or S; q is 1, 2, or 3; and $R^2$ and $R^3$ each, independently, are either H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, or $(CH_2)_n$—O—$(CH_2)_n$ where n is 1–10. Alternatively, $R^2$ and $R^3$ together form a ring structure or a substituted ring structure.

Other preferred compounds of the invention have Formula V:

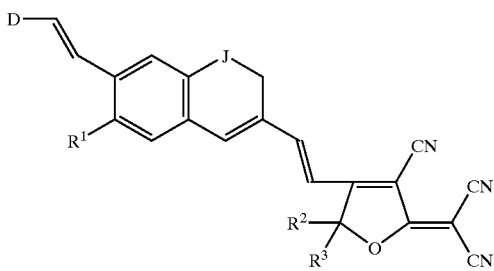

V wherein D is an electron donating group; J is $CH_2$, O or S; $R^1$ is —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q is absent, O or S; and $R^2$ and $R^3$ each, independently, are either H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, or $(CH_2)_n$—O—$(CH_2)_n$ where n is 1–10. Alternatively, $R^2$ and $R^3$ together form a ring structure or a substituted ring structure.

The present invention is also directed to optical waveguides comprising a thin film medium having Formula VI:

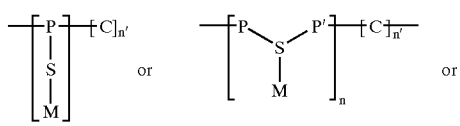

VI

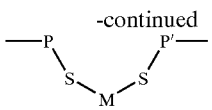

wherein P and P' are polymer main chain units, which can be the same mer unit or different mer unit, and C is a comonomer unit where n is an integer greater than zero and n' is 0 or an integer greater than zero; S is a pendant spacer group having a linear chain length of between about 2–12 atoms. M is a compound having either Formula I, Formula II, Formula III, Formula IV, or Formula V, as described above.

The chromophores of the present invention have several advantageous features which are not found in other known or commercially available chromophores. The electro-optic chromophores of the invention exhibit thermal stability to temperatures from 260° C. to 310° C. The chromophores of the invention also show great solubility in most common organic solvents and, thus, are useful in most polymer films for waveguides. In addition, under intense UV-irradiation (365 nm, dosage 3 J/cm² up to 13 minutes), the chromophores of the invention show no changes of the UV-VIS-NIR spectrum, which indicates that the chromophores are photo stable. The chromophores of the present invention also demonstrate an adjustable absorption band away from normal communications wavelenghts, which can be very important for reducing optical loss at communication wavelengths. The chromophores of the invention have significant three-dimensional design which can prevent chromophore-chromophore anti-parallel stacking. Because of the flexible side chain substitutions, the chromophores of the invention show significantly reduced birefringence losses. In some of the chromophores of the invention, there is unique regiospecific substitution on the bridging thiophene ring, which allows the electron acceptor to more easily access the conjugated π system of the bridge and allows the molecule backbone to be flatter. In addition, some of the preferred chromophores of the invention have hydroxyl groups on the electron donor termini in order to easily process the chromophore into hydroxyl compatible organic and inorganic polymer reactions to make soluble chromophores, polymers and copolymers, as well as can be used to make highly soluble "guest" chromophores for guest-host applications.

The present invention is also directed to optical devices comprising the optical waveguides described above.

DESCRIPTION OF PREFERRED EMBODIMENTS OF THE INVENTION

The present invention is directed, in part, to novel electro-optic chromophores which have utility in organic nonlinear optical applications. The chromophores of the invention can be used in, for example, polymeric thin films for optical waveguides and optical devices. Such polymeric thin films are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety.

The phrase "electron donating group" is used synonymously with "electron donator" and refers to substituents which contribute electron density to the π-electron system when the conjugated electron structure is polarized by the input of electromagnetic energy.

The phrase "electron withdrawing group" is used synonymously with "electron accepting group" and "electron acceptor" and refers to electronegative organic compounds or substituents which attract electron density from the π-electron system when the conjugated electron structure is polarized by the input of electromagnetic energy.

The term "chromophore" as used herein refers to an optical compound comprising an electron donating group and an electron withdrawing group at opposing termini of a conjugated π electron system.

The phrase "cyclic bridge" is used to refer to bivalent cyclic structures which serve to couple the electron donating and withdrawing groups.

The present invention is directed, in part, to compounds which can be employed as chromophores in polymeric thin films for optical waveguides. In preferred embodiments of the invention, compounds comprise novel electron withdrawing groups and have Formula I:

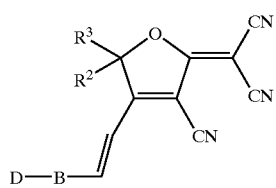

D is an electron donating group. Preferred electron donating groups are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. Preferably, D is selected from the group consisting of, but not limited to, phenyl ring(s) substituted in the para position by, for example, amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, 1,2,3,4-tetrahydroquinolinyl, and the like. The most preferred electron donating group are substituted and unsubstituted—phenyl-N(CH$_2$CH$_2$OH)$_2$.

B is a cyclic bridge which couples the electron withdrawing group and the electron donating group. Preferably, B is at least one bivalent ring. Preferred cyclic bridges comprise one or a plurality of bivalent rings. Preferred bivalent rings which can be employed as cyclic bridges in the present application are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. Ring B can be aromatic or non-aromatic. Preferably, B is selected from the group consisting of, but not limited to,

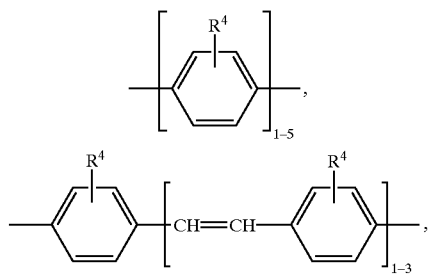

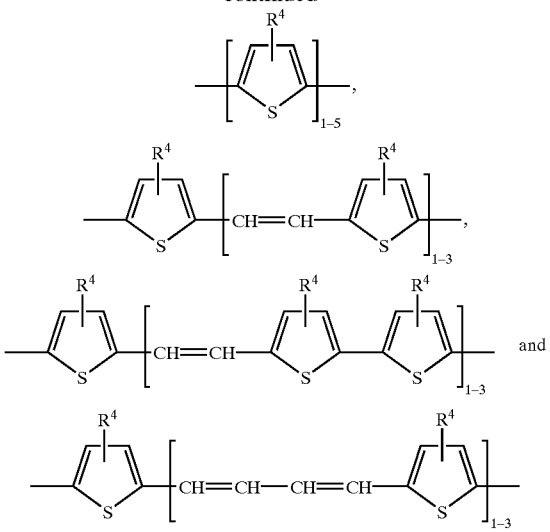

where $R^4$ is H, OH, $C_1$–$C_{10}$ alkyl, alkenyl, or alkynyl, halogen, and the like. $R^4$ can also be —Q—$C_nH_{2n+1}$, —Q—(CH$_2$)$_a$C$_n$F$_{2n+1}$, —Q—CH$_2$OCH$_2$C$_n$F$_{2+1}$, —Q—CH$_2$SCH$_2$CC$_n$F$_{2n+1}$, —Q—CH$_2$OCH$_2$CF$_3$, or —Q—CH$_2$SCH$_2$CF$_3$, where n is 1–10, a is 0–10, and Q is absent, O or S; and q is 1, 2, or 3.

Preferably, $R^2$ and $R^3$ each, independently, are selected from the group consisting of, but not limited to, H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, (CH$_2$)$_n$—O—(CH$_2$)$_n$ where n is 1–10, and the like. "$C_1$–$C_{10}$" refers to $C_1$, $C_2$, $C_3$, $C_4$, $C_5$, $C_6$, $C_7$, $C_8$, $C_9$, $C_{10}$, and all combinations of ranges thereof.

The substituted alkyl, alkenyl, alkynyl, carbocyclic, and heterocyclic groups can comprise one or a plurality of substituents including, for example, fluorine, chlorine, D, and the like. In addition, the heterocyclic groups can comprise O, N, S, and the like.

The aryl groups preferably include, but are not limited to, benzyl, phenyl, fluorenyl, and naphthyl. The aryl groups, carbocycles, heterocycles, and cyclohexyl can also be substituted by one or a plurality of substituents including, for example, D, halides, including fluorine, chlorine and bromine. The alkylaryl groups preferably comprise $C_1$–$C_{10}$ alkyl and the substituted alkylaryl groups comprise the substitutions for the alkyl and aryl groups described above.

In more preferred embodiments of the invention, $R^2$ and $R^3$ each, independently, are selected from the group consisting of benzyl, carbocycle, heterocycle, cyclohexyl, phenyl, cycloalkyl, cycloalkenyl, and substituted phenyl. Additional moieties for $R^1$ and/or $R^2$, independently, include, but are not limited to the following:

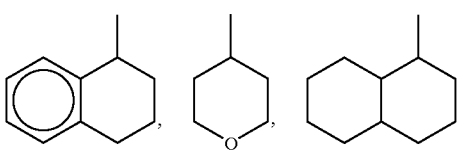

and the like.

In even more preferred embodiments of the invention, one of $R^2$ and $R^3$ is $CH_3$ and the other of $R^2$ and $R^3$ is a substituted phenyl. Preferably, the substituted phenyl is selected from the group consisting of, but not limited to:

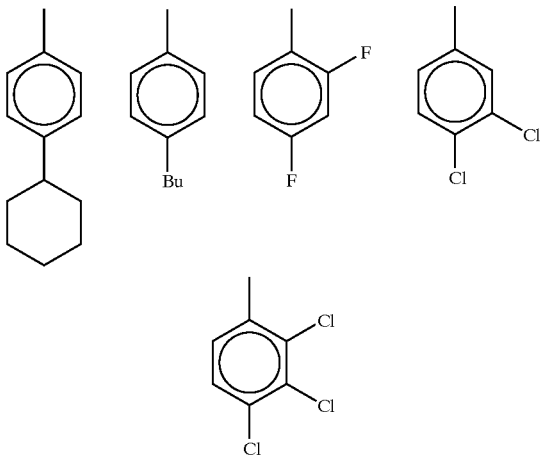

and the like.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl or cyclopentyl. The substituted ring structure can comprise substituents including, but not limited to, halides, including fluorine, chlorine and bromine. A preferred compound having a ring structure formed by $R^2$ and $R^3$ comprises

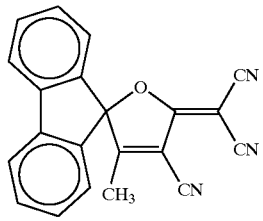

The electron withdrawing groups of the present invention are preferably prepared according to Scheme I:

Scheme I

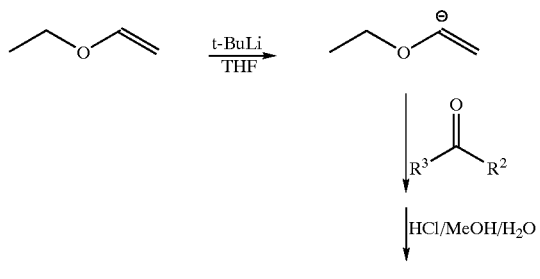

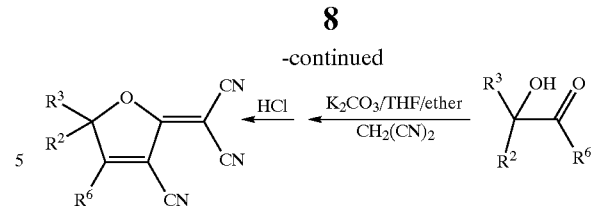

Compounds having Formula I are preferably prepared by the following steps depicted in Scheme I: a) providing an alkylvinylether, b) contacting the alkylvinylether with a strong base to form a first intermediate compound, c) contacting the first intermediate compound with a ketone to form a second intermediate compound, and d) reacting the second intermediate compound with dicyanomethane in the presence of a second base to form an electron withdrawing group portion of a compound having Formula I. Each of the above mentioned steps is described in greater detail below.

In preferred embodiments of the invention, an alkylvinylether in a solvent is the starting material. The solvent is, preferably, tetrahydrofuran (THF), 1,4-dioxane, or the like. Although the alkylvinylether depicted in Scheme I is ethylvinylether, other alkylvinylethers can be used. The alkylvinylether preferably comprises the formula $CH_3-(CH_2)_x-O-CH=CHR^6$, where x is 1-3 and $R^6$ is $C_1-C_4$ alkyl. Most preferably, the alkylvinylether is methylvinylether or ethylvinylether.

The alkylvinylether is contacted with a strong base to form a first intermediate compound. Preferably, the strong base has a $pK_a$ greater than the ethylinic C-H bond α to the oxygen function of the alkylvinylether. For example, see Advanced Organic Chemistry, Third Ed., Jerry March, 1985, Table 1, pp. 220-222. In preferred embodiments of the invention, the strong base is an alkyl lithium, or an alkali metal salt of an alkyl anion, including, but not limited to, t-BuLi or sec-BuLi. The alkylvinylether is preferably contacted with the strong base between about -70° C. and -85° C., most preferably at about -78° C.

The first intermediate compound is contacted with a ketone and an acid/alcohol/water solution to form a second intermediate compound. Numerous acid/alcohol/water solutions known to those skilled in the art can be used in the present invention. The acid/alcohol/water solution is preferably $HCl/MeOH/H_2O$, $HBr/EtOH/H2O$, or $H_2SO4/EtOH/H_2O$. Preferably, the contacting is at room temperature. Preferably, the pH is adjusted between 1 and 4.

Preferably, the ketone comprises $R^3-C(=O)R^2$, wherein $R^2$ and $R^3$ each, independently, are selected from the group consisting of H, substituted and unsubstituted $C_1-C_{10}$ alkyl, substituted and unsubstituted $C_1-C_{10}$ alkenyl, substituted and unsubstituted $C_1-C_{10}$ alkynyl, substituted and unsubstituted aryl, substituted and unsubstituted alkylaryl, substituted and unsubstituted carbocycle, substituted and unsubstituted heterocycle, substituted and unsubstituted cyclohexyl, and $(CH_2)_n-O-(CH_2)_n$ where n is 1-10.

"$C_1-C_{10}$" refers to $C_1$, $C_2$, $C_3$, $C_4$, $C_5$, $C_6$, $C_7$, $C_8$, $C_9$, $C_{10}$, and all combinations ranges thereof.

Preferably, the C=C and C≡C bonds of the alkenyl and alkynyl groups are not immediately adjacent or conjugated to the carbonyl group of the ketone compound.

The substituted alkyl, alkenyl, alkynyl, carbocyclic, and heterocyclic groups can comprise one or a plurality of substituents including, for example, fluorine, chlorine, D, and the like. In addition, the heterocyclic groups can comprise O, N, S, and the like.

The aryl groups preferably include, but are not limited to, benzyl, phenyl, fluorenyl, and naphthyl. The aryl groups, carbocycles, heterocycles, and cyclohexyl can also be substituted by one or a plurality of substituents including, for example, D, halides, including fluorine, chlorine and bromine. The alkylaryl groups preferably comprise $C_1$–$C_{10}$ alkyl and the substituted alkylaryl groups comprise the substitutions for the alkyl and aryl groups described above.

In more preferred embodiments of the invention, $R^2$ and $R^3$ each, independently, are selected from the group consisting of benzyl, carbocycle, heterocycle, cyclohexyl, phenyl, cycloalkyl, cycloalkenyl, and substituted phenyl. Additional moieties for $R^1$ and/or $R^2$, independently, include, but are not limited to the following:

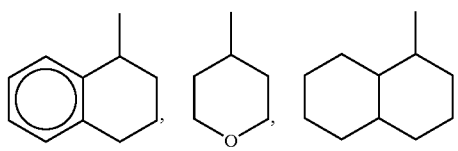

and the like.

In even more preferred embodiments of the invention, one of $R^2$ and $R^3$ is $CH_3$ and the other of $R^2$ and $R^3$ is a substituted phenyl. Preferably, the substituted phenyl is selected from the group consisting of, but not limited to:

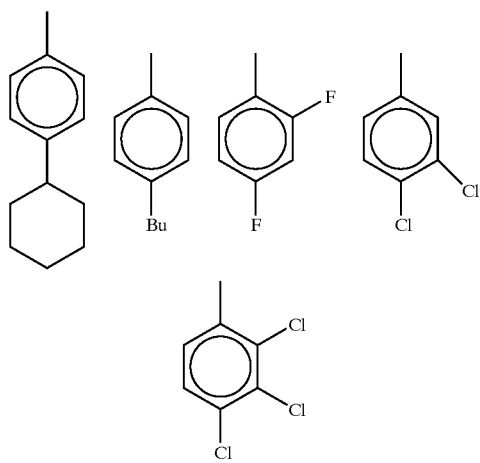

and the like.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl or cyclopentyl. The substituted ring structure can comprise substituents including, but not limited to, halides, including fluorine, chlorine and bromine. A preferred compound having a ring structure formed by $R^2$ and $R^3$ comprises

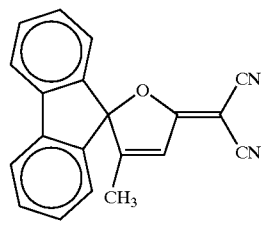

The second intermediate compound is reacted with dicyanomethane in the presence of a second base to form the electron withdrawing group portion of a compound having Formula I. The second base is preferably a metal alkoxide including, but not limited to, $NaOC_2H_5$. After contacting the second intermediate compound with dicyanomethane in the presence of a second base, dilute acid such as, for example, HCl, is added for neutralization of the resultant electron withdrawing group.

The electron withdrawing group comprises $R^6$ which is preferably selected from the group consisting of unbranched substituted or unsubstituted $C_1$–$C_4$ alkyl, unbranched substituted or unsubstituted $C_2$–$C_4$ alkenyl, unbranched substituted or unsubstituted $C_2$–$C_4$ alkynyl. The substituted alkyl, alkenyl, and alkynyl groups can comprise one or a plurality of substituents including, for example, fluorine. In preferred embodiments of the invention, $R^6$ is selected from the group consisting of unbranched $C_1$–$C_4$ alkyl, $C_1$–$C_4$ alkenyl, and $C_1$–$C_4$ alkynyl. In more preferred embodiments of the invention, $R^6$ is $CH_3$.

The present invention is also directed, in part, to compounds which can be employed as chromophores in polymeric thin films for optical waveguides wherein the compounds comprise novel bridge groups which couple the electron withdrawing and donating groups of the chromophore. Preferred compounds of the invention have Formula II:

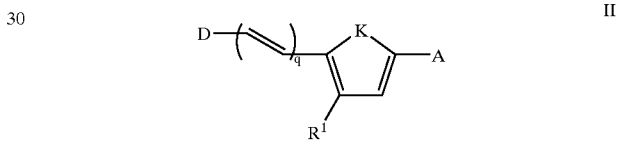

II

D is an electron donating group. Preferred electron donating groups are described above.

A is an electron withdrawing group. Preferred electron withdrawing groups are described in, for example, U.S. Pat. Nos. 5,044,725, 4,795,664, 5,247,042, 5,196,509, 4,810, 338, 4,936,645, 4,767,169, 5,326,661, 5,187,234, 5,170,461, 5,133,037, 5,106,211, and 5,006,285, each of which is incorporated herein by reference in its entirety. Preferably, A is selected from the group of molecular units containing, but not limited to, nitro, cyano, haloalkyl, acyl, carboxy, aryloxy, carboxamido, alkoxysulfonyl, aryloxysulfonyl, —CH=C(CN)$_2$, —C(CN)=C(CN)$_2$, SO$_2$CF$_3$, alkanoyloxy,

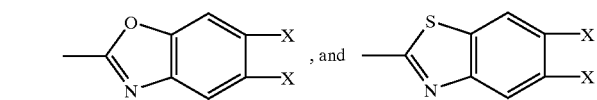

, and where X is H, D, F, CN, NO$_2$, or CF$_3$.

$R^1$ is —Q—$C_nH_{2n+1}$, —Q—$(CH_2)_aC_nF_{2n+1}$, —Q—$CH_2OCH_2C_nF_{2n+1}$, —Q—$CH_2SCH_2CC_nF_{2n+1}$, —Q—$CH_2OCH_2CF_3$, or —Q—$CH_2SCH_2CF_3$, where n is 1–10, a is 0–10, and Q preferably either absent or, when present, O or S; q is 1, 2, or 3. More preferably, $R^1$ is $C_4$–$C_{10}$ or fluorine substituted $C_{4-10}$.

A compound having Formula II can be prepared using a thiophene cyclic bridge which preferably comprises Formula VII:

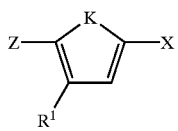

Preferably, K is O or S.

Preferably, $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q preferably is either absent or, when present, O or S. Other halogens or deuterium can be used in place of F. In more preferred embodiments of the invention, $R^1$ is $C_4$–$C_{10}$ or fluorine substituted $C_4$–$C_{10}$.

X preferably has the formula $-(CH=CH)_b-C(=O)H$, where b is 0–3. The terminal aldehyde group serves as the preferred site of reaction with electron withdrawing groups. In more preferred embodiments of the invention, b is 0 so that X is $-C(=O)H$.

Z is a chemical group that is capable of being linked to a donor and includes, but is not limited to, Br, I, $-CH_2-Br$, $-CH_2-OH$, $-CH_3$, $-C(=O)H$, and the like. Those skilled in the art can use additional groups known to those skilled in the art to couple a bridge compound to a donor. Another Z group that can be used to link a bridge compound to a donor is

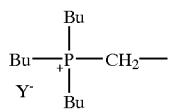

where Y⁻ is a counter ion including, but not limied to, Br⁻ or Cl⁻.

In other embodiments of the invention, preferred compounds of the invention have Formula III:

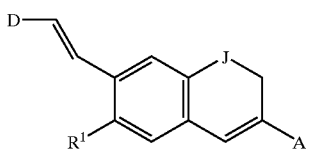

D is an electron donating group and A is an electron withdrawing group as described above. 3 is $CH_2$, O Or S. $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S. More preferably, $R^1$ is $C_4$–$C_{10}$ or fluorine substituted $C_4$–$C_{10}$.

A compound having Formula IV can be prepared using a dihydronaphthyl cyclic bridge which preferably comprises Formula VIII:

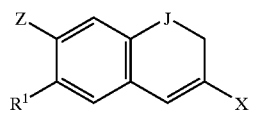

Preferably, J is $CH_2$, O or S.

Preferably, $R^1$ is H, $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S. Other halogens can be used in place of F. In more preferred embodiments of the invention, $R^1$ is $C_4$–$C_{10}$ or fluorine substituted $C_4$–$C_{10}$.

X preferably has the formula (C=O)H or C=CH($-CH=CH)_d-C(=O)H$, where d is 0–3. The terminal aldehyde or ketone group serves as the preferred site of reaction with electron withdrawing groups. In more preferred embodiments of the invention, X is (C=O)H.

Z is a chemical group that is capable of being linked to a donor, as described above.

The present invention is also directed, in part, to compounds which can be employed as chromophores in polymeric thin films for optical waveguides wherein the compounds comprise novel bridge groups and novel electron withdrawing groups. Preferred compounds of the invention have Formula IV:

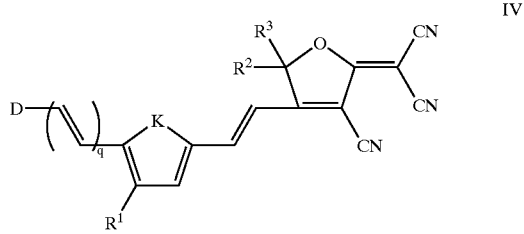

K is O or S.

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S, and q is 1, 2, or 3. In more preferred embodiments of the invention, $R^1$ is $C_4$–$C_{10}$ or fluorine substituted $C_4$–$C_{10}$.

Preferably, $R^2$ and $R^3$ each, independently, are selected from the group consisting of, but not limited to, H; substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, $(CH_2)_n-O-(CH_2)_n$ where n is 1–10, and the like. More preferably, $R^2$ and $R^3$ each, independently, are selected from the group consisting of substituted or unsubstituted aryl, substituted or unsubstituted alkylaryl, and substituted or unsubstituted cyclohexyl. More preferably, $R^2$ and $R^3$ each, independently, are selected from the group consisting of benzyl, cyclohexyl, and substituted or unsubstituted phenyl. More preferably, one of $R^2$ and $R^3$ is $CH_3$ and the other of $R^2$ and $R^3$ is a substituted phenyl. Most preferably, one of $R^2$ and $R^3$ is

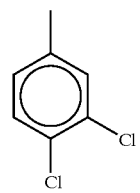

and the other of $R^2$ and $R^3$ is $CH_3$.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl or cyclopentyl. The substituted ring structure can comprise substituents including, but not limited to, deuterium and halides, including fluorine, chlorine and bromine. A preferred compound having a ring structure formed by $R^2$ and $R^3$ comprises

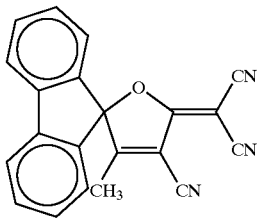

D is an electron donating group as described above.

In other embodiments of the invention, preferred compounds have Formula V:

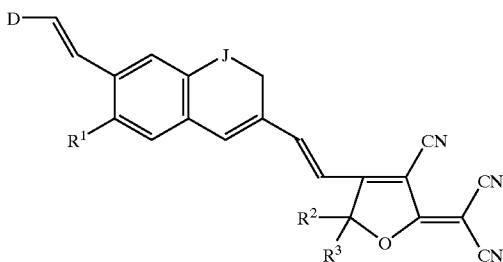

J is $CH_2$, O or S.

Preferably, $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S. In more preferred embodiments of the invention, $R^1$ is $C_4-C_{10}$ or fluorine substituted $C_4-C_{10}$.

Preferably, $R^2$ and $R^3$ each, independently, are selected from the group consisting of, but not limited to, H, substituted or unsubstituted $C_1-C_{10}$ alkyl, substituted or unsubstituted $C_2-C_{10}$ alkenyl, substituted or unsubstituted $C_2-C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, $(CH_2)_n-O-(CH_2)_n$ where n is 1–10, and the like. More preferably, $R^2$ and $R^3$ each, independently, are selected from the group consisting of substituted or unsubstituted aryl, substituted or unsubstituted alkylaryl, and substituted or unsubstituted cyclohexyl. More preferably, $R^2$ and $R^3$ each, independently, are selected from the group consisting of benzyl, cyclohexyl, and substituted or unsubstituted phenyl. More preferably, one of $R^2$ and $R^3$ is $CH_3$ and the other of $R^2$ and $R^3$ is a substituted phenyl. Most preferably, one of $R^2$ and $R^3$ is

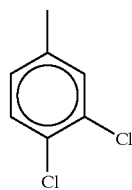

and the other of $R^2$ and $R^3$ is $CH_3$.

Alternatively, $R^2$ and $R^3$ together form a ring structure or a substituted ring structure from 3 to 7 atoms total with 5 or 6 atoms being preferred. Preferably, the ring structure is substituted or unsubstituted carbocycle, substituted or unsubstituted heterocycle, or substituted or unsubstituted cyclohexyl. The substituted ring structure can comprise substituents including, but not limited to, deuterium and halides, including fluorine, chlorine and bromine. A preferred compound having a ring structure formed by $R^2$ and $R^3$ comprises

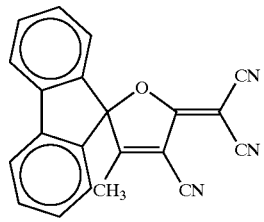

D is an electron donating group as described above.

The present invention is also directed, in part, to optical waveguides comprising polymeric this films having comprising the chromophores of the invention. In preferred embodiments of the invention, optical waveguides comprising a thin film medium have Formula VI:

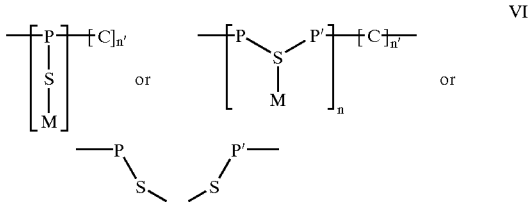

P and P' are polymer main chain units, which can be the same mer unit or different mer unit, and C is a comonomer unit where n is an integer greater than zero and n' is 0 or an integer greater than zero. Polymers and copolymers that may be employed in the present invention are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. The polymers of the invention can be a homopolymer or a copolymer. Preferred polymers and copolymers include, but are not limited to, acrylate, vinyl carboxylate, substituted arylvinyl, vinyl halide, vinyl carboxylate, alkene, alkadiene, arylvinyl, methacrylate, vinyl chloride, vinyl acetate, vinyl ether, ethylene, propylene, isobutylene, 1-butene, isoprene, styrene, and the like.

Preferably, the polymers of the invention comprise an external field-induced orientation and alignment of pendant side chains. Preferably, the polymer main chain can be a structural type such as polyvinyl, polyoxyalkylene, polysiloxane, polycondensation, and the like. A polymer can be applied to a supporting substrate by conventional means, such as spin coating, dip coating, spraying, Langmuir-Blodgett deposition, and the like. Thin film optical waveguide medium of the present invention after fabrication can be subjected to an external field to orient and align uniaxially the polymer side chains. In one method the polymer medium is heated close to or above the polymer glass transition temperature $T_g$, then an external field (e.g., a DC electric field) is applied to the medium of mobile chromophore molecules to induce uniaxial molecular alignment of the chromophore polymer side chains or guests in a guest-host system parallel to the applied field, and the medium is cooled while maintaining the external field effect.

S is a pendant spacer group having a linear chain length of between about 2–12 atoms. Pendant spacer groups that may be employed in the present invention are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety.

M is a chromophore compound having Formula I, Formula II, Formula III, Formula IV, or Formula V, described above.

The present invention is also directed, in part, to optical devices comprising the optical waveguides of the invention. Optical devices are described in, for example, U.S. Pat. Nos. 5,044,725, 4,795,664, 5,247,042, 5,196,509, 4,810,338, 4,936,645, 4,767,169, 5,326,661, 5,187,234, 5,170,461, 5,133,037, 5,106,211, and 5,006,285, each of which is incorporated herein by reference in its entirety. Preferred optical devices include, but are not limited to, laser frequency converters, optical interferometric waveguide gates, wideband electrooptical guided wave analog-to-digital converters, optical parametric devices, and the like, as described in U.S. Pat. No. 4,775,215, which is incorporated herein by reference in its entirety.

The invention is further illustrated by way of the following examples which are intended to elucidate the invention. These examples are not intended, nor are they to be construed, as limiting the scope of the disclosure.

EXAMPLES

Example 1

General Synthesis Of Dicyanomethylenedihydrofurans

To a solution of 0.33 mol of ethyl vinyl ether in 150ml of dry THF, 0.3mol of t-BuLi in pentane was added dropwise at −78° C. The mixture was stirred and allowed to warm up slowly to 0° C. and subsequently cooled to −78° C. again. Next, 0.25 mol of cyclohexyl phenyl ketone dissolved in a minimum of dry THF was added dropwise. The mixture was stirred overnight at room temperature, then acidified using HCl/MeOH/THF/H$_2$O solution to pH 1–4. After stirring this mixture for two hours, most of the solution was evaporated using a rotary evaporator. The remaining mixture was extracted with ethyl ether (3×100 ml). The organic solution was washed with NaHCO$_3$, brine, and DI water. This mixture was then dried over anhydrous MgSO$_4$. After evaporating the ether, the crude product was purified by column chromatography (5% ethyl acetate in hexane) to give pure alpha-hydroxy ketone (30 g).

The hydroxy ketone synthesized above (0.02 mol) was mixed with malononitrile (0.04 mol) in ethyl alcohol at 20% w/v based on malononitrile cooled in an ice bath. To this, 20 ml of 1 M NaOC$_2$H$_5$/EtOH was added dropwise. The mixture was allowed to stir overnight. After neutralization by concentrated HCl to pH 6, the solvent was evaporated by vacuum. The residue was dissolved into CH$_2$Cl$_2$ and filtered to remove the undissolved solid. After evaporating the CH$_2$Cl$_2$, the crude product was purified by recrystalization from ethanol to give the dicyanomethylenedihydrofuran compound (1.25 g).

Alternatively, and more preferably, the hydroxy ketone synthesized above (0.02 mol) was mixed with malononitrile (0.04 mol) and potassium. carbonate (0.02 mol) in THF (40 ml) and EtOH (2 ml). To this mixture, a catalytic amount of 18-crown ether was added. The mixture was stirred and allowed to reflux overnight. The solid was filtered off, followed by evaporation of most of the solvent. The crude mixture was purified by column chromatography (CH$_2$Cl$_2$) to give the dicyanomethylenedihydrofuran compound (1.5 g) shown below (melting point, MP=194–196° C.).

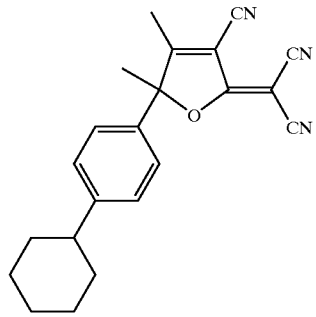

Example 2

Preparation of a Dicyanomethylenedihydrofuran-based Electron Acceptor

To a solution of ethylvinylether (28.8 g in 300 ml of TBF) was added 176 ml of t-BuLi dropwise at −78° C. The mixture was slowly warmed to ODC and subsequently cooled to −78° C. again. Cyclohexanone (30 g in 30 ml of THF) was added dropwise and the mixture was slowly warmed to room temperature and stirred for an additional four hours. A solution of methanol (70 ml), water (20 ml) and conc. HCl (10 ml) was slowly added to the reaction mixture until a pH of about 2–3 was obtained. The mixture was stirred overnight and neutralized to pH 7by addition of a 20% solution of NaHCO$_3$ in water and the solvent was evaporated. The residual solvent was extracted by ether (3×100 Ml). The ether solution was washed with NaHCO$_3$ (50 ml), brine (100 ml), and dried over anhydrous MgSO$_4$. After removal of the ether, vacuum distillation of the intermediate fielded 36 g.

CH$_2$(CN)$_2$(13.2 g) and a 1 M solution of NaOC$_2$H$_5$(0.1 mole) were mixed in an ice bath. Approximately 14.2 g of the intermediate prepared as described above and dissolved in a minimum of EtOH was added dropwise and stirred overnight at room temperature. The mixture was neutralized by 8 ml of conc. HCl to a pH of 6.0 and the solid material was filtered off and the remaining solution was evaporated. The residue from the solution was dissolved into CH$_2$Cl$_2$, filtered again, followed by evaporating the CH$_2$Cl$_2$. The rest of the mixture was recrystalized from ethanol (150 ml) to give 6.1 g of the final compound shown below (mMP=239–241° C.).

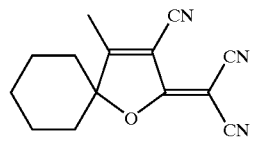

Example 3

Preparation of a Dicyanomethylenedihydrofuran-based Electron Acceptor

To a solution of ethylvinylether (21.6 g in 300 ml of THF) was added 110 ml of t-BuLi dropwise at −78° C. The mixture was warmed to 0° C. and subsequently cooled to −78° C. again. 5', 4'-dichloroacetophenone (30.5 g) was dissolved into 150 ml of THF and then added dropwise. This mixture was run overnight at room temperature. A solution of HCl (10 ml), methanol (70 ml), and water (20 ml) was added to the reaction the next day. The mixture was adjusted to pH 4 and allowed to stir overnight. NaHCO$_3$ was added to neutralize this solution to pH 7. The mixture was extracted by ether (3×100 ml). The combined organic acid mixture was washed with NaHCO$_3$(50 ml), brine (100 ml), and dried over anhydrous MgSO$_4$. Vacuum distillation of the intermediate yielded 55 g.

CH$_2$(CN)$_2$ (13.2 g) and a 1 M solution of NaOC$_2$H$_5$ (0.1 mole) were mixed in an ice bath. Approximately 15 g of the intermediate prepared as described above and dissolved in EtOH was added dropwise and stirred overnight at room temperature. The mixture was neutralized by 8 ml of conc. HCL to a pH of 6.0 and the solid material was filtered and the resulting solution evaporated. The residue was dissolved into CH$_2$Cl$_2$, filtered again, followed by evaporating the CH$_2$Cl$_2$. The rest of the mixture was recrystalized from ethanol (150 ml) to give 5.5 g of the final compound shown below (MP=110–111° C.; 152–153° C.; and 222–224° C., respectively left to right).

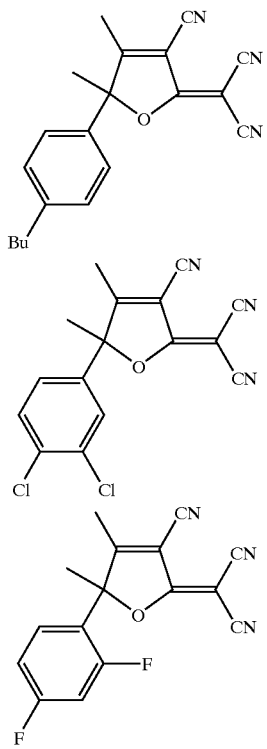

Example 4

Preparation of trans-[(N,N-di(2-ethanol)amino) phenylene-3-decanyl-2-thiophene]

To a solution of 3-decanyl-2-methyltributylphosphonium-thiophene bromide (26 g, 0.05 mol) and N,N-di-ethanol aminophenyl aldehyde (12.6 g, 0.06 mol) in 200 ml of ethanol, NaOC$_2$H$_5$ (1 M in ethanol) was added dropwise. The resulting mixture was refluxed for 98 hours. After removal of this reaction from the bath oil, the solvent was evaporated, and the residue was extracted with ethyl ether (3×150 ml). The combined ether mixture was washed with water (100 ml), brine (2×100 ml) and dried over anhydrous MgSO$_4$. After removal of the solvent, the residue was purified by column chromatography on silica and eluted using 50% ethyl acetate, 10% acetone, and 40% hexane to give the pure title compound with a yield of 16 g. Carbon and proton NMR were consistent with the structure.

Example 5

Preparation of trans-[(N,N-di(2-ethanol)amino) phenylene-2-thiene-3-decanyl-5-al]

To a 500 ml flask with the compound synthesized above (10.44 g, 0.0243 mol), 200 ml of THF was added. The solution was cooled to −78° C. and n-BuLi (32 ml, 2.5M in hexane) was added dropwise. The mixture was stirred for 2 hours followed by addition of DMF (6 ml). The resulting solution was stirred overnight at room temperature. After adding HCl (2 M, 50 ml) and stirring for an hour, the THF was evaporated. The residue was extracted with ethyl ether (3×100 ml). The combined organic solution was washed with saturated Na$_2$CO$_3$ solution (50 ml), water (100 ml), brine (100 ml) and dried over anhydrous MgSO$_4$. After evaporating the solvent, solid target compound (11.1 g, mp 107–109° C.) was obtained. HNMR showed that this compound was pure enough for the next step.

Example 6

Preparation of Chromophore

The above aldehyde compound (3 g, 6.54 mmol) and 2-dicyanomethylen-3-cyano-4,5-dimethy-5-(3,4-dichlorophenyl)-2,5-dihydrofuran (2.4 g, 7.27 mmol) were mixed and dissolved in EtOH (30 ml). Two or three drops of piperidine were added. The mixture was refluxed for 48 hours. After cooling, the precipitated solid was filtered, recrystalized from EtOH, and purified by chromatography silica elution solvent to give 3.38 g of the chromophore. Carbon and proton NMR were performed and analysis thereof was consistent with the structure.

Example 7

Preparation of Chromophore

Trans-[(N,N-di(2-ethanol)amino)phenylene-3,4-dibutyl-2-thiophene-5-al] (0.3 g, 0.7 mmol) is mixed with 2-dicyanomethylen-3-cyano-4,5-dimethyl-5-(3,4-dichlorophenyl)-2,5-dihydrofurane (0.23 g, 0.7 mmol) in EtOH (20 ml). Two or three drops of piperidine is added. The mixture is refluxed for 48 hours. After cooling, the precipitated solid is filtered, recrystalized from EtOH, and purified by chromatography silica elution solvent.

Example 8

Preparation of Highly Chlorinated Electro-Optic Polymer

To a three-neck flask with 1,4,5,6,7,7-hexchloro-5-norbornene-2,3-dicarboxylic acid chloride (2.65 g, 6.23 mmol) and 2,3,5,6-tetrachloro-p-xylene-αα-diol (1.36 g, 4.93 mmol), 2-dicyanomethylen-3-cyano-4-{2-[E-(4-N,N-di-(2-ethanol)amino)phenylene-(3-decanyl)thien-5]-E-vinyl}-5-methyl-5-(3,4-dichlorophenyl)-2,5-dihydrofuran (1 g, 1.3 mmol) were mixed in 20 ml THF at 70° C. Et$_3$N (1.26 g in 15 ml THF) was added dropwise. The mixture was refluxed under Ar for 48 hours. After evaporating some of the THF, the rest of the solution was slowly dropped into MeOH (300 ml) and water (50 ml) with violent stirring. The precipitated solid was filtered, redissolved in THF and precipitated again in MeOH (300 ml). The collected solid was vacuum dried for 8 hours and weighed 4.5 g. The polymer was characterized by DSC and TGA. The $T_g$ is 152° C., and the decomposing temperature under air is 285° C.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A compound having Formula I:

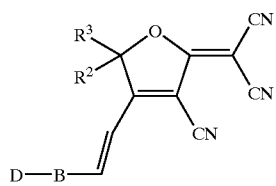

I wherein:

D is an electron donating group;

B comprises at least one bivalent ring;

$R^2$ is selected from the group consisting of H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is 1–10; and $R^3$ is selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is 1–10;

or $R^2$ and $R^3$ together form a ring structure or a substituted ring structure.

2. The compound of claim 1 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

3. The compound of claim 2 wherein B is selected from the group consisting of

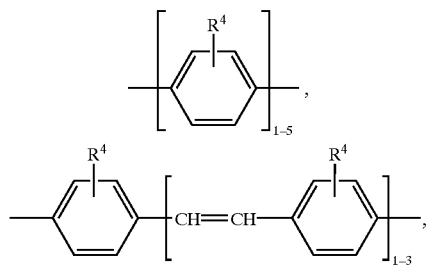

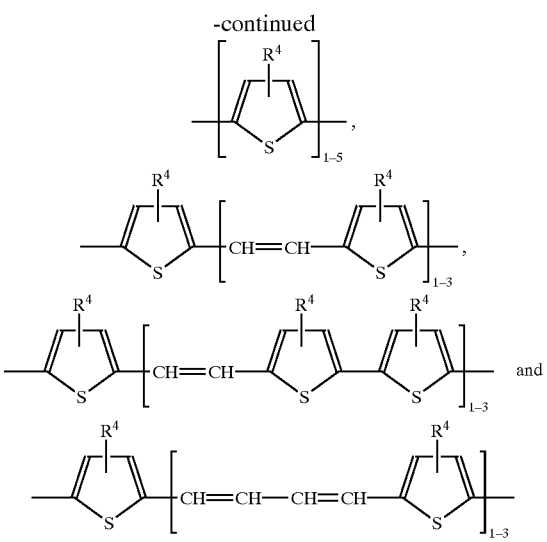

where $R^4$ is H, OH, $C_1$–$C_{10}$ alkyl, alkenyl, alkynyl, or halogen.

4. The compound of claim 1 wherein $R^2$ and $R^3$ each, independently, are selected from the group consisting of substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is 1–10.

5. The compound of claim 4 wherein $R^2$ and $R^3$ are the same.

6. The compound of clam 1 wherein $R^2$ and $R^3$ each, independently, are selected from the group consisting of benzyl, cyclohexyl, cyclopentyl, and substituted or unsubstituted phenyl.

7. The compound of claim 6 wherein one of $R^2$ and $R^3$ is $CH_3$ and the other of $R^2$ and $R^3$ is a substituted phenyl.

8. The compound of claim 7 wherein the substituted phenyl is

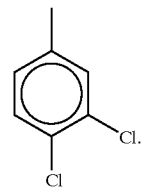

9. The compound of claim 1 wherein $R^2$ and $R^3$ together form a ring structure or a substituted ring structure.

10. The compound of claim 9 wherein $R^2$ and $R^3$ together form cyclohexyl or cyclopentyl.

11. An optical waveguide comprising a thin film medium having Formula VI

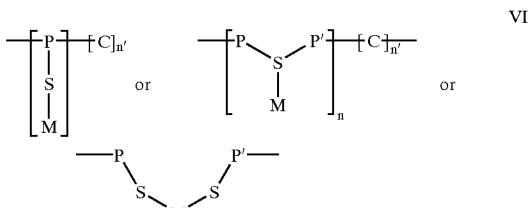

VI wherein:

P and P' are polymer main chain units;

C is a comonomer unit;

S is a pendant spacer group having a linear chain length of between about 2–12 atoms;

n is an integer greater than zero;

n' is 0 or an integer greater than zero; and

M is a compound according to claim 1.

12. An optical device comprising the optical waveguide of claim 11.

13. The optical device of claim 12 wherein said device is selected from the group consisting of a laser frequency converter, an optical interferometric waveguide gate, a wideband electrooptical guided wave analog-to-digital converter, and an optical parametric device.

14. A compound having Formula II

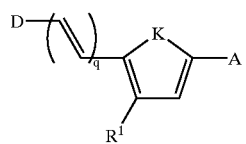

II wherein:

K is O or S;

D is an electron donating group;

A is an electron accepting group;

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; and q is 1, 2, or 3.

15. The compound of claim 14 wherein is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

16. The compound of claim 15 wherein A comprises a molecular unit selected from the group consisting of nitro, cyano, haloalkyl, acyl, carboxy, aryloxy, carboxamido, alkoxysulfonyl, aryloxysulfonyl, $-CH=C(CN)_2$, $-C(CN)=C(CN)_2$, $SO_2CF_3$, alkanoyloxy,

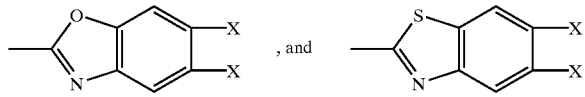

where X is H, D, F, CN, $NO_2$, or $CF_3$.

17. The compound of claim 16 wherein a is 1–3 and n is 1–3.

18. The compound of claim 17 wherein $R^1$ is $C_4-C_{10}$ or fluorine substituted $C_4-C_{10}$.

19. A compound having Formula III

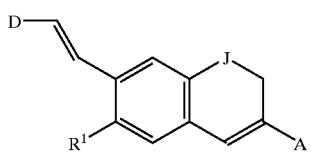

III wherein:

J is $CH_2$, O or S;

D is an electron donating group;

A is an electron accepting group; and $R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S.

20. The compound of claim 19 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

21. The compound of claim 20 wherein a is 1–3 and n is 1–3.

22. The compound of claim 21 wherein $R^1$ is $C_4-C_{10}$ or fluorine substituted $C_4-C_{10}$.

23. The compound of claim 19 wherein A comprises a molecular unit selected from the group consisting of nitro, cyano, haloalkyl, acyl, carboxy, aryloxy, carboxamido, alkoxysulfonyl, aryloxysulfonyl, $-CH=C(CN)_2$, $-C(CN)=C(CN)_2$, $SO_2CF_3$, alkanoyloxy,

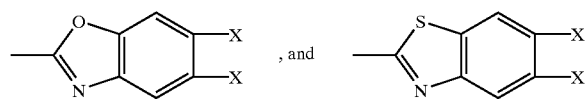

where X is H, D, F, CN, $NO_2$, or $CF_3$.

24. An optical waveguide comprising a thin film medium having Formula VI

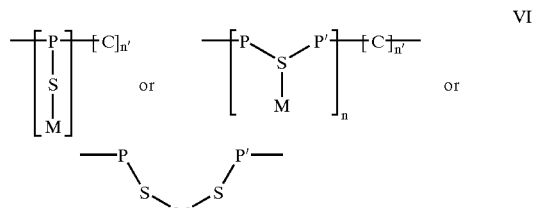

VI wherein:

P and P' are polymer main chain units;

C is a comonomer unit;

S is a pendant spacer group having a linear chain length of between about 2–12 atoms;

n is an integer greater than zero;

n' is 0 or an integer greater than zero; and

M is a compound of claim 14 or 19.

25. An optical device comprising the optical waveguide of claim 24.

26. The optical device of claim 25 wherein said device is selected from the group consisting of a laser frequency converter, an optical interferometric waveguide gate, a wideband electrooptical guided wave analog-to-digital converter, and an optical parametric device.

27. A compound having Formula IV

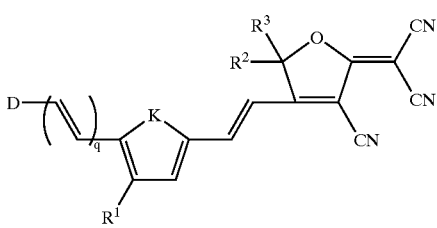

wherein:

D is an electron donating group;

K is O or S;

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{12n+1}$, $-Q-CH_2OCH_2CF_3$, or $-Q-CH_2SCH_2CF_3$, where n is 1–10, a is 0–10, and Q is absent, O or S;

q is 1, 2, or 3; and $R^2$ and $R^3$ each, independently, are selected from the group consisting of H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10; or $R^2$ and $R^3$ together form a ring structure or a substituted ring structure.

28. The compound of claim 27 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

29. The compound of claim 28 wherein $R^2$ and $R^3$ each, independently, are selected from the group consisting of H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10.

30. The compound of claim 29 wherein $R^2$ and $R^3$ each, independently, are selected from the group consisting of substituted or unsubstituted aryl, substituted or unsubstituted alkylaryl, and substituted or unsubstituted cyclohexyl or cyclopentyl.

31. The compound of claim 30 wherein $R^2$ and $R^3$ each, independently, are selected from the group consisting of benzyl, cyclohexyl, cyclopentyl, and substituted or unsubstituted phenyl.

32. The compound of claim 31 wherein one of $R^2$ and $R^3$ is $CH_3$ and the other of $R^2$ and $R^3$ is a substituted phenyl.

33. The compound of claim 32 wherein the substituted phenyl is

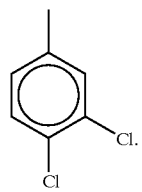

34. The compound of claim 29 wherein a is 1–3 and n is 1–3.

35. The compound of claim 34 wherein $R^1$ is $C_4$–$C_{10}$ or fluorine substituted $C_4$–$C_{10}$.

36. The compound of claim 35 wherein $R^2$ and $R^3$ together form cyclohexyl or cyclopentyl.

37. The compound of claim 28 therein $R^2$ and $R^3$ together form a ring structure or a substituted ring structure.

38. The compound of claim 37 wherein a is 1–3 and n is 1–3.

39. The compound of claim 38 wherein $R^1$ is $C_4$–$C_{10}$ or fluorine substituted $C_4$–$C_{10}$.

40. A compound having Formula V

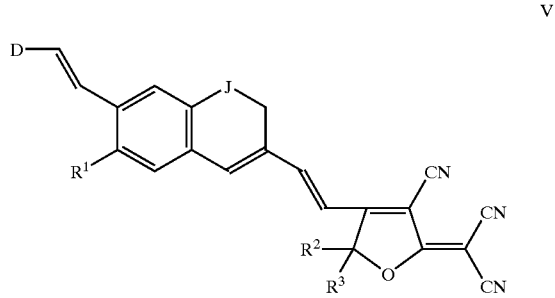

wherein:

D is an electron donating group;

J is $CH_2$, O or S;

$R^1$ is $-Q-C_nH_{2n+1}$, $-Q-(CH_2)_aC_nF_{2n+1}$, $-Q-CH_2OCH_2C_nF_{2n+1}$, $-Q-CH_2SCH_2CC_nF_{2n+1}$, $-Q-CH_2OCH_2CF_3$, or $-Q-CH_2SCH_2CF_3$, where n is 1–10, a is 0–10, and Q is absent, O or S; and $R^2$ and $R^3$ each, independently, are selected from the group consisting of H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n-O-(CH_2)_n$ where n is 1–10; or $R^2$ and $R^3$ together form a ring structure or a substituted ring structure.

41. The compound of claim 40 wherein D is a phenyl ring substituted at the para position by a moiety selected from the group consisting of amino, alkylamino, dialkylamino, dialkylanilino, 1-piperidino, 1-piperazino, 1-pyrrolidino, acylamino, hydroxyl, thiolo, alkylthio, arylthio, alkoxy, aryloxy, acyloxy, alkyl, vinyl, and 1,2,3,4-tetrahydroquinolinyl.

42. The compound of claim 41 wherein $R^2$ and $R^3$ each, independently, are selected from the group consisting of H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is 1–10.

43. The compound of claim 42 wherein $R^2$ and $R^3$ each, independently, are selected from the group consisting of substituted or unsubstituted aryl, substituted or unsubstituted alkylaryl, substituted or unsubstituted carbocycle, substituted or unsubstituted heterocycle, and substituted or unsubstituted cyclohexyl.

44. The compound of claim 43 wherein $R^2$ and $R^3$ each, independently, are selected from the group consisting of benzyl, cyclohexyl, cyclopentyl, and substituted or unsubstituted phenyl.

45. The compound of claim 44 wherein one of $R^2$ and $R^3$ is $CH_3$ and the other of $R^2$ and $R^3$ is a substituted phenyl.

46. The compound of claim 45 wherein the substituted phenyl is

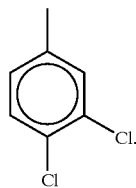

In accordance with 37 C.F.R. 01.121 (c) (1) (ii), a marked-up version of the claims amended above showing the changes relative to the claims pending immediately prior to the present amendment is attached hereto in an addendum entitled "ADDENDUM TO AMENDMENT DATED NOV. 2, 2001". In this addendum, deletions are indicated by square brackets and insertions are indicated by underlining.

47. The compound of claim 46 wherein a is 1–3 and n is 1–3.

48. The compound of claim 47 wherein $R^1$ is $C_4$–$C_{10}$ or fluorine substituted $C_4$–$C_{10}$.

49. The compound of claim 41 wherein $R^2$ and $R^3$ together form a ring structure or a substituted ring structure.

50. The compound of claim 49 wherein $R^2$ and $R^3$ together form cyclohexyl or cyclopentyl.

51. The compound of claim 50 wherein a is 1–3 and n is 1–3.

52. The compound of claim 51 wherein $R^1$ is $C_4$–$C_{10}$ or fluorine substituted $C_4$–$C_{10}$.

53. An optical waveguide comprising a thin film medium having Formula VI

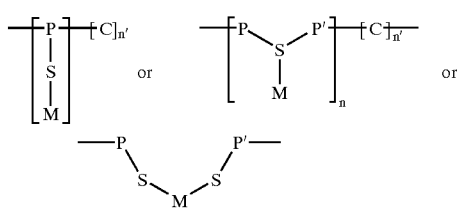

wherein:
P and P' are polymer main chain units;

C is a comonomer unit;
S is a pendant spacer group having a linear chain length of between about 2–12 atoms;
n is an integer greater than zero;
n' is 0 or an integer greater than zero; and
M is a compound of claim 27 or 40.

54. An optical device comprising the optical waveguide of claim 53.

55. The optical device of claim 54 wherein said device is selected from the group consisting of a laser frequency converter, an optical interferometric waveguide gate, a wideband electrooptical guided wave analog-to-digital converter, and an optical parametric device.

56. A method of preparing an electron withdrawing group comprising the steps:
(a) providing an alkylvinylether;
(b) contacting said alkylvinylether with a strong base to form a first intermediate compound;
(c) contacting said first intermediate compound with a ketone to form a second intermediate compound; and
(d) reacting said second intermediate compound with dicyanomethane in the presence of a second base to form said electron withdrawing group.

57. The method of claim 56 wherein said alkylvinylether is in a solvent.

58. The method of claim 57 wherein said solvent is tetrahydrofuran or 1,4-dioxane.

59. The method of 56 wherein said alkylvinylether comprises the formula $CH_3$—$(CH_2)_x$—O—$CH$=$CHR^6$, where x is 1–3 and $R^6$ is H or $C_1$–$C_4$ alkyl.

60. The method of claim 59 wherein said alkylvinylether is methylvinylether or ethylvinylether.

61. The method of claim 56 wherein said strong base has a $pK_a$ greater than the ethylinic C-H bond a to the oxygen function of said alkylvinylether.

62. The method of claim 61 wherein said strong base is an alkyl lithium.

63. The method of claim 62 wherein said alkyl lithium is t-BuLi or sec-BuLi.

64. The method of claim 56 wherein said ketone comprises the formula $R^3$—$C(=O)R^2$, wherein $R^2$ and $R^3$ each, independently, are selected from the group consisting of H, substituted or unsubstituted $C_1$–$C_{10}$ alkyl, substituted or unsubstituted $C_2$–$C_{10}$ alkenyl, substituted or unsubstituted $C_2$–$C_{10}$ alkynyl, substituted or unsubstituted aryl, substituted or unsubstituted alkylaryl, substituted or unsubstituted carbocycle, substituted or unsubstituted heterocycle, substituted or unsubstituted cyclohexyl, and $(CH_2)_n$—O—$(CH_2)_n$ where n is 1–10.

65. The method of claim 64 wherein said $R^2$ and $R^3$ each, independently, are selected from the group consisting of benzyl, cyclohexyl, cyclopentyl, phenyl, and substituted phenyl.

66. The method of claim 65 wherein one of said $R^2$ and $R^3$ is $CH_3$ and the other of $R^2$ and $R^3$ is a substituted phenyl.

67. The method of claim 56 wherein said second base is a metal alkoxide.

68. The method of claim 67 wherein said metal alkoxide is $NaOC_2H_5$.

* * * * *